US012797818B2

(12) United States Patent
Adam et al.

(10) Patent No.: US 12,797,818 B2

(45) Date of Patent: Nov. 17, 2026

(54) DEVICE FOR AEROSOL GENERATION AND USE OF A DEVICE FOR AEROSOL GENERATION

(71) Applicant: TOPAS GMBH TECHNOLOGIE-ORIENTIERTE PARTIKEL-, ANALYSEN- UND SENSORTECHNIK, Dresden (DE)

(72) Inventors: René Adam, Dresden (DE); Franziska Nowak, Dresden (DE); Andreas Rudolph, Dresden (DE)

(73) Assignee: TOPAS GMBH TECHNOLOGIE-ORIENTIERTE PARTIKEL-, ANALYSEN- UND SENSORTECHNIK, Dresden (DE)

( * ) Notice: Subject to any disclaimer, the term of this patent is extended or adjusted under 35 U.S.C. 154(b) by 656 days.

(21) Appl. No.: 18/264,388

(22) PCT Filed: Dec. 28, 2021

(86) PCT No.: PCT/EP2021/087730

§ 371 (c)(1),
(2) Date: Aug. 4, 2023

(87) PCT Pub. No.: WO2022/171352

PCT Pub. Date: Aug. 18, 2022

(65) Prior Publication Data

US 2024/0042409 A1 Feb. 8, 2024

(30) Foreign Application Priority Data

Feb. 10, 2021 (DE) ........................ 10 2021 103 107

(51) Int. Cl.

| | |
|---|---|
| ***B01J 13/00*** | (2006.01) |
| ***A61M 11/00*** | (2006.01) |
| ***A61M 11/02*** | (2006.01) |

(52) U.S. Cl.

CPC ........ *B01J 13/0095* (2013.01); *A61M 11/002* (2014.02); *A61M 11/02* (2013.01)

(58) Field of Classification Search

CPC .......... A61M 11/001-003; A61M 11/02; B01J 13/0095; B05B 7/24; B05B 7/2489; B05B 14/00; B05B 1/28

See application file for complete search history.

(56) References Cited

U.S. PATENT DOCUMENTS 2,998,391 A * 8/1961 Jones .................. B01J 13/0095 47/DIG. 12

3,838,686 A * 10/1974 Szekely ................ B05B 7/0012 239/338

(Continued)

FOREIGN PATENT DOCUMENTS

AU 713700 B2 12/1999

CA 2827093 A1 * 3/2014 ............ A61M 35/25

(Continued)

OTHER PUBLICATIONS

International Search Report and Written Opinion of International Application No. PCT/EP2021/087730, mailed on Apr. 8, 2022, 14 pages. Full translation.

*Primary Examiner* — Kathryn E Ditmer

(74) *Attorney, Agent, or Firm* — HESLIN ROTHENBERG FARLEY & MESITI P.C.

(57) ABSTRACT

The invention relates to devices for aerosol generation comprising a container holding a liquid, an aerosol generator having a supply container holding the liquid, and an apparatus for conditioning the aerosol of the aerosol generator, said apparatus having a collection container for liquid and an outlet for the aerosol, in a series connection, wherein the aerosol generator is connected to a pressurized gas generator. The invention also relates to uses of such devices. Said devices and uses are characterized in particular by interrup- (Continued)

tion-free operation. For this purpose, the collection container is connected to the aerosol generator via a first non-return valve in the passage direction and via a first jet pump, wherein the opening pressure of the first non-return valve is smaller than the pressure that can be achieved by the first jet pump. Furthermore, the container is connected to the aerosol generator via a second non-return valve in the passage direction and via a second jet pump, wherein the opening pressure of the second non-return valve is greater than the pressure difference between the supply container of the aerosol generator and the surroundings of the device for aerosol generation and smaller than the pressure that can be achieved by the second jet pump.

14 Claims, 1 Drawing Sheet

(56) References Cited

U.S. PATENT DOCUMENTS

| | | | | | |
|---|---|---|---|---|---|
| 4,943,007 | A * | 7/1990 | Bowe | B05B 1/26 | 261/115 |
| 5,213,117 | A * | 5/1993 | Yamamoto | B08B 3/08 | 134/58 DL |
| 5,261,949 | A * | 11/1993 | Schilling | F23K 5/22 | 95/227 |
| 5,277,175 | A * | 1/1994 | Riggs | A61M 16/0858 | 128/203.14 |
| 5,320,108 | A | 6/1994 | Cloutier | | |
| 5,800,598 | A * | 9/1998 | Chein | A61M 11/001 | 55/318 |
| 7,201,163 | B2 * | 4/2007 | Jiang | A61M 16/142 | 128/200.14 |
| 7,641,130 | B2 * | 1/2010 | Ricciardi | B05B 7/0012 | 239/102.1 |
| 2004/0244792 | A1 * | 12/2004 | Hashiba | A61M 11/06 | 128/200.21 |
| 2005/0042170 | A1 * | 2/2005 | Jiang | A61M 16/14 | 128/200.23 |
| 2009/0001198 | A1 * | 1/2009 | Norimatsu | B05B 7/1445 | 239/654 |
| 2010/0044474 | A1 * | 2/2010 | Allen | B05B 5/025 | 239/690 |
| 2012/0227820 | A1 * | 9/2012 | Poster | F01M 5/001 | 184/6 |
| 2013/0281919 | A1 * | 10/2013 | Nakamura | A61H 33/028 | 604/24 |
| 2014/0109899 | A1 * | 4/2014 | Boucher | A61M 11/003 | 128/200.14 |
| 2014/0115765 | A1 * | 5/2014 | Carpenter | A61L 9/14 | 4/223 |
| 2015/0313275 | A1 | 11/2015 | Anderson et al. | | |
| 2018/0001408 | A1 * | 1/2018 | Hayashi | B05B 7/0075 | |
| 2018/0272377 | A1 * | 9/2018 | Sadri | B05C 11/1039 | |

FOREIGN PATENT DOCUMENTS

| | | | | |
|---|---|---|---|---|
| CN | 1083396 | A * | 3/1994 | A61M 11/002 |
| DE | 4040227 | A1 | 6/1992 | |
| DE | 102017219370 | B3 | 12/2018 | |
| JP | 2001082685 | A * | 3/2001 | B05B 7/0012 |
| WO | WO-03008106 | A1 * | 1/2003 | B05B 1/26 |
| WO | WO-2018065586 | A1 * | 4/2018 | B08B 17/00 |
| WO | 2020180236 | A1 | 9/2020 | |

* cited by examiner

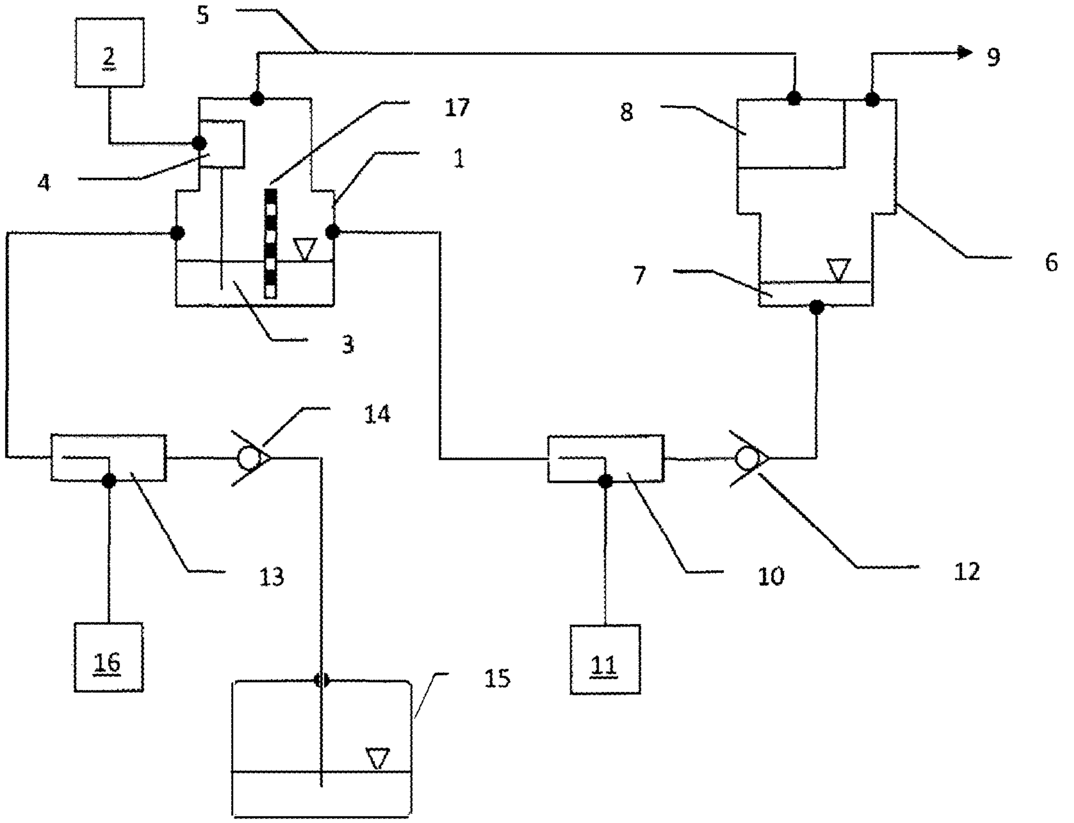
5
2
9
17
8
1
4
6
7
3
14
13
10
12
16
15
11

DEVICE FOR AEROSOL GENERATION AND USE OF A DEVICE FOR AEROSOL GENERATION

CROSS REFERENCE TO RELATED APPLICATIONS

This application is a national stage filing under section 371 of International Application No. PCT/EP2021/087730, filed on Dec. 28, 2021, and published on Aug. 18, 2022 as WO 2022/171352, which claims priority to German Application No. 10 2021 103 107.9, filed on Feb. 10, 2021. The entire contents of WO 2022/171352 are hereby incorporated by reference herein.

The invention relates to devices for aerosol generation, comprising a container holding a liquid, an aerosol generator having a supply container holding the liquid, and an apparatus for conditioning, having a collection container for holding the particles of the aerosol of the aerosol generator separated as liquid, and having an outlet of the aerosol, in a series connection, wherein the aerosol generator is connected to a pressurized gas generator; and to uses of a device for aerosol generation.

Known aerosol generators are used, for example, to spray liquid using pressurized gas. The document DE 10 2017 219 370 B3 discloses a device for generating an aerosol of solid particles from a liquid supply container by means of cold nebulization. The device has an atomizing nozzle with a downstream impact separator, which is further connected to the atomizing nozzle via a liquid supply container and a pump. The liquid pump is used for the recirculation. The compatibility of materials, and the not-inconsiderable effort complexity, are disadvantageous. Furthermore, the quantity of liquid to be recirculated is unknown and is not constant over time. In addition, in particular the intermittent movement of liquid and gas is also problematic since the nominal delivery capacity of the liquid pump must be greater than the maximum quantity of liquid to be discharged.

The publication U.S. Pat. No. 5,320,108 A also discloses an improved generator of aerosol particles for use in inhalation. For this purpose, the generator comprises means for continuously suspending a certain amount of specific particles in a pressurized air stream in order to produce a compressed aerosol of a particular composition. For this purpose, a suction pump is used in conjunction with a valve for regulating the delivery flow of the suction pump.

WO 2020/180 236 A1 describes a method and an apparatus for cleaning an air flow of particles. For this purpose, an aerosol of liquid droplets is mixed with the air flow. The liquid droplets are separated with the particles using a downstream separator.

The publication DE 40 40 227 A1 discloses a powder mist generator with a powder container for holding a powder bed, with a jet pump which is connected with a suction opening to the head space of the powder container lying above the powder bed and can be connected to the surrounding environment via an at least partially closable secondary air opening, and with releasing means for releasing powder from the exposed surface of the powder bed. A refill line is connected to the interior of the powder container. The jet pump serves to mix a powder-rich premix with a large carrier-air gas stream. By means of a secondary air opening in the jet pump, the volume of the carrier gas flow, and thus the suction of the powder-rich pre-mist from the interior of the powder container, can be limited. Thus, the refilling of powder is simplified and a powder mist with very low powder concentration can be produced.

The object of the invention is to provide a device for aerosol generation which can be operated without interruption.

This object is achieved by the features listed in the independent claims.

The devices according to the invention for aerosol generation, comprising a container holding a liquid, an aerosol generator having a supply container holding the liquid, and an apparatus for conditioning, having a collection container for holding the particles of the aerosol of the aerosol generator separated as liquid, and having an outlet of the aerosol, in a series connection, wherein the aerosol generator is connected to a pressurized gas generator, and the uses thereof, are characterized in particular by the fact that they can be operated without interruption.

For this purpose, the collection container is connected to the aerosol generator via a first non-return valve in the passage direction and via a first jet pump. Furthermore, the container is connected to the aerosol generator via a second non-return valve in the passage direction and via a second jet pump, wherein the opening pressure of the second non-return valve is greater than the pressure difference between the supply container of the aerosol generator and the surroundings of the device for aerosol generation and smaller than the pressure that can be achieved by the second jet pump.

The collection container is connected via the first non-return valve in the passage direction, and via the first jet pump, to the aerosol generator in such a way that the opening pressure of the first non-return valve is smaller than the pressure that can be achieved by the first jet pump. Furthermore, the opening pressure of the second non-return valve is greater than the pressure difference between the supply container of the aerosol generator and the surroundings of the device for aerosol generation and smaller than the pressure that can be achieved by the second jet pump. If these conditions are met, liquid does not flow through the connection between the aerosol generator and the container into the container, or out of the container, even if it is opened, for example for refilling liquid into the container. This is also the case if the supply of pressurized gas for the second jet pump is shut off. It is accordingly very simple to refill liquid into the supply container of the aerosol generator from the container by hand. The container can thus also be filled during operation.

For industrial quality assurance, systems for producing aerosols with particles in a gas stream are also used, for example, for filter testing. Because of the separation behavior of filters being tested, typically selective for particle size, there are special demands for the test aerosol with respect to particle size distribution and particle concentration. Comparable requirements also arise from the behavior of the particle measurement technology, selective for particle size, that is essential for the filter test.

Devices for aerosol generation can have an aerosol generator and a downstream apparatus for conditioning the aerosol with respect to the particle size distribution and particle concentration of the aerosol.

Known aerosol generators are used, for example, to spray liquid using pressurized gas. For this purpose, the material for the particles can be situated in a supply container in the aerosol generator, so that the supply container is a component of the aerosol generator. As a result, excessively large droplets which occur during the generation process can be separated out, and the liquid obtained in this case can be returned to the supply container by gravity.

The functional principle of the downstream apparatus for the conditioning of the aerosol always consists of a size-selective separation of particles from the aerosol stream generated by the aerosol generator.

Devices for aerosol generation are frequently used in continuous operation. Accordingly, separation mechanisms in which the separated particles are not stored long-term, are preferably used in the conditioning process. The continuous operation is thus ensured without having to change a used separating element. As a result of this separation process, the material of the separated particles is present in the form of a liquid in the collection container. A specific characteristic of such separators is always a differential pressure between the outlet at a low pressure and the inlet at a higher pressure. This pressure difference is an expression of the energy required for the separation.

Thus, it is not easily possible to move this liquid, which is materially identical to the liquid in the supply container of the aerosol generator, back into the same. Advantageously, the device for aerosol generation makes this possible, so that excessive consumption from the supply container of the aerosol generator can be prevented. At the same time, liquid obtained in the apparatus for conditioning the aerosol of the aerosol generator does not have to be discarded.

For the recirculation, a known liquid pump could be used. The compatibility of materials, and the not-inconsiderable effort complexity, are disadvantageous. Furthermore, the quantity of liquid to be recirculated is unknown and is not constant over time. In addition, in particular the intermittent movement of liquid and gas is also problematic since the nominal delivery capacity of the liquid pump must be greater than the maximum quantity of liquid to be discharged. Accordingly, the device for aerosol generation advantageously implements the recirculation with the first jet pump, which contains no mechanically moving parts and is particularly resistant to failure. The propellant gas flow occurring during the pumping process is admixed to the aerosol and reduces the concentration of the aerosol.

The recirculation of the liquid which is separated in the apparatus for conditioning the aerosol of the aerosol generator has the effect that the removal from the supply container of the aerosol generator is not excessive. However, the dispensing of the conditioned aerosol continuously decreases the fill level in the supply container of the aerosol generator with increasing operating time. Interruption-free operation is only possible by refilling liquid.

This refilling is not possible by a simple and manual filling of the supply container of the aerosol generator during operation. This is because of the pressure difference of the connection of the aerosol delivery and the atmospheric pressure of the surrounding environment of the device used for aerosol generation, which is always present in practice. This leads to the requirement for a hermetic seal for both the aerosol generation and the conditioning during operation. If the hermetic seal is compromised during operation, however, undesirably either aerosol enters the surrounding environment or ambient air enters in. "Hermetic" in this case means air-tight, which means that hermetic sealing is the process of sealing to prevent material exchange. For refilling the aerosol generator from the container, the second jet pump is therefore used.

The particular advantage of the resistance of the jet pump to failure is balanced by the disadvantage of unhindered fluid passage between the inlet and the outlet when the propellant gas is shut off. For refilling, this would result in a loss of the hermetic seal of the device for aerosol generation, and for the recirculation, this would result in a flow of unconditioned aerosol to the outlet for the conditioned aerosol. Therefore, the non-return valves connected in series with the jet pumps are present in the passage direction. In this way, an intermittent operation of the jet pumps is likewise possible, which minimizes the mean volume flow of propellant gas. Thus, the lowest possible dilution of the aerosol is achieved. Devices for pressurized gas supply are connected to the jet pumps, so that the propellant gas for the jet pumps can thereby be supplied.

The opening pressure of the non-return valve is selected in each case such that the achievable pressure difference at the jet pumps is greater, and the overall effective pressure difference is less. The fluid connection is thus shut off in the event of the pressurized gas of the jet pumps being switched off. In the event of the pressurized gas being switched on, liquid is conveyed.

The device for aerosol generation, which is thus easily realized, is characterized in that, on the one hand, the liquid from the collection container of the apparatus for conditioning is conveyed back into the supply container of the associated aerosol generator, against the prevailing pressure difference, and in that, as well, the refilling of liquid into the supply container of the aerosol generator from the container with liquid can take place easily by hand even during ongoing operation. The device for aerosol generation is thus operable and usable without interruption.

Advantageous embodiments of the invention are specified in the dependent claims.

In embodiments of the invention, the aerosol generator has a self-priming two-component nozzle. In this case, liquid is sprayed with pressurized gas, wherein the droplets carried in the gas have a spherical shape as particles. Furthermore, the self-priming two-component nozzle is characterized by a simple implementation.

In embodiments of the invention, the self-priming two-component nozzle is arranged in a chamber, wherein the supply container is a component of the chamber. In the process of generating the aerosol, excessively large droplets are separated out, and the liquid obtained can return to the supply container by gravity. The supply container is advantageously such a component of the aerosol generator.

In embodiments of the invention, the apparatus for conditioning the aerosol advantageously has a separator for selecting the size of particles from the aerosol stream generated by the aerosol generator.

In embodiments of the invention, the apparatus for conditioning the aerosol, with the separator, is connected via the first non-return valve and the first jet pump to the aerosol generator, such that the separator is a separator which does not provide long-term storage for the separated particles.

In embodiments of the invention, the separator with a short-term storage of separated particles is a cyclone separator or a coalescent fiber separator.

In embodiments of the invention, the separator and the collection container are optionally the components of a further chamber, such that the particles separated as liquid pass into the collection container by gravity.

In embodiments of the invention, the first jet pump is a first injector pump, and the second jet pump is a second injector pump. They are advantageously pressurized-gas-operated injector pumps.

In embodiments of the invention, an actuating device of an apparatus for operating the aerosol generator, an actuating device of an apparatus for operating the first jet pump, and an actuating device of an apparatus for operating the second jet pump are connected to a control device.

In embodiments of the invention, the supply container, the collection container and/or the container has or have a fill level sensor or fill level sensors, which is or are connected to a control device.

Advantageously, the actuating device of the apparatus for operating the aerosol generator, the actuating device of the apparatus for operating the first jet pump, the actuating device of the apparatus for operating the second jet pump, and the fill level sensor or the fill level sensors are connected to a control device. This results in a reliable continuous operation of the device for aerosol generation even over a longer period of time. Accordingly, for the refilling procedure, the control device can be coupled to the liquid fill level sensor arranged in the supply container. In this way, the jet pump can be put into operation for the refilling procedure if the fill level drops below a certain fill level and can be shut down when a certain fill level is exceeded. In this way, a fill level of the aerosol generator within certain limits can be ensured during long-term operation. In conjunction with the fill level sensor in the container, this can also be ensured over a longer time span. For signaling a necessary manual refilling of liquid into the container, the control device can be connected to a known signaling device.

The invention also relates to the use of the device for aerosol generation according to the invention, for the uninterrupted generation of aerosols, for example for industrial quality assurance and for filter tests.

In order to realize the invention, it is also expedient to combine the above-described embodiments and the features of the claims.

The invention is explained in more detail below with reference to an exemplary embodiment and associated FIGURE. The exemplary embodiment is intended to describe the invention without limiting it.

In the drawings:

FIG. 1 shows a device for aerosol generation.

A device for aerosol generation is substantially made up of a container 15 holding a liquid, an aerosol generator 1 with a supply container 3 holding the liquid, an apparatus 6 for conditioning the aerosol of the aerosol generator 1 with a collection container 7 of liquid and an outlet of the aerosol, a first non-return valve 12, a first jet pump 10, a second jet pump 13, and a second non-return valve 14.

The aerosol generator 1 used for spraying the slightly volatile liquid by means of pressurized gas has a self-priming two-component nozzle 4 which is connected via a hose to the liquid of the supply container 3, as a further component of the aerosol generator 1. For spraying liquid, the two-component nozzle 4 is connected to a first device 2 for the pressurized gas supply.

The aerosol generator 1 is connected via an aerosol-carrying connection 5 to the apparatus 6 for conditioning the aerosol, which is provided at the outlet 9 of the apparatus 6 for conditioning. This apparatus has a size-selective separator 8 of particles from the aerosol stream generated by the aerosol generator 1. For example, the separator 8 can be a cyclone separator 8 or a coalescent fiber separator 8. A further component of the apparatus 6 for conditioning is the collection container 7 for holding the particles separated as a liquid. The collection container 7 (at the lowest point thereof, in this case) and the supply container 3 of the aerosol generator 1 are connected to one another via a fluid-conducting connection, in which are arranged, as seen proceeding from the collection container 7, a first non-return valve 12 in the passage direction and a first jet pump 10 in the form of a pressurized-gas-operated injector pump 10. The opening pressure of the first non-return valve 12 is less than the negative pressure achievable by the first injector pump 10. In this way, the liquid is conveyed back out of the collection container against the prevailing pressure difference to the apparatus 6 for conditioning the aerosol of the aerosol generator 1. For this purpose, the first pressurized-gas-operated injector pump 10 is connected to a second device 11 for the pressurized gas supply.

Furthermore, there is a fluid-conducting connection between the container 15 with liquid and the supply container 3. In this connection, viewed in order from the container 15, are situated a second non-return valve 14 in the passage direction and a second jet pump 13 as a pressurized-gas-operated injector pump 13. The opening pressure of the second non-return valve 14 is greater than the pressure difference between the supply container 3 of the aerosol generator 1 and the surrounding environment of the device for aerosol generation, and less than the negative pressure achievable by the second injector pump 13. If these conditions are met, liquid does not flow through the connection between the aerosol generator 1 and the container 15 into or out of the container 15, even when it is opened, for example for refilling liquid into the container 15, even if the supply of pressurized gas for the second injector pump 13 is shut off. The refilling of liquid into the supply container 3 of the aerosol generator 1 from the container 15 is thus easily possible by hand. It can thus even be filled during operation. The second pressurized-gas-operated injector pump 13 is connected to a third device 16 for supplying pressurized gas.

An actuating device of an apparatus for operating the aerosol generator 1, an actuating device of an apparatus for operating the first jet pump 10, and an actuating device of an apparatus for operating the second jet pump 13 can be connected to a control device. Furthermore, the supply container 3, the collection container 7, and/or the container 15 can have a fill level sensor 17 or fill level sensors 17 which is or are connected to a control device or the control device. FIG. 1 shows, by way of example, a fill level sensor 17 in the supply container 3.

REFERENCE SIGNS

1 aerosol generator
2 first device for the pressurized gas supply
3 supply container
4 two-component nozzle
5 aerosol-carrying connection
6 apparatus for conditioning
7 collection container
8 separator, cyclone separator, or coalescent fiber separator
9 outlet
10 first jet pump, first injector pump
11 second device for the pressurized gas supply
12 first non-return valve
13 second jet pump, second injector pump
14 second non-return valve
15 container
16 third device for the pressurized gas supply
17 fill level sensor

The invention claimed is:

1. A device for aerosol generation, comprising:
a container holding a liquid,
an aerosol generator with a supply container holding the same liquid, and
an apparatus for conditioning with a collection container for receiving particles of an aerosol of the aerosol generator separated as liquid, and an outlet for the aerosol, wherein the container, the aerosol generator, the apparatus for conditioning and the outlet are in a series connection, wherein the aerosol generator is connected to a pressurized gas generator, wherein the collection container is connected to the aerosol generator via a first non-return valve, configured to allow flow in a passage direction from the collection container to the aerosol generator, and a first jet pump, and wherein the container is connected to the aerosol generator via a second non-return valve, configured to allow flow in a passage direction from the container to the aerosol generator, and a second jet pump, wherein the second non-return valve is configured such that its opening pressure is greater than the pressure difference between the supply container of the aerosol generator and the surroundings of the device for aerosol generation and smaller than a pressure difference generated by the second jet pump during operation.

2. The device for aerosol generation according to claim 1, wherein the aerosol generator has a self-priming two-component nozzle.

3. The device for aerosol generation according to claim 2, wherein the self-priming two-component nozzle is arranged in a chamber, and in that the supply container is a component of the chamber, such that droplets that occur in the process of generating the aerosol which are too large are separated out, and the liquid obtained in the process returns to the supply container by gravity.

4. The device for aerosol generation according to claim 2, wherein the apparatus for conditioning the aerosol has a separator for selecting a size of particles from an aerosol stream generated by the aerosol generator.

5. The device for aerosol generation according to claim 2, wherein the first jet pump is a first injector pump, and the second jet pump is a second injector pump.

6. The device for aerosol generation according to claim 1, wherein the aerosol generator has a nozzle arranged in a chamber, and in that the supply container is a component of the chamber, such that droplets that occur in the process of generating the aerosol which are too large are separated out, and the liquid obtained in the process returns to the supply container by gravity.

7. The device e for aerosol generation according to claim 1, wherein the apparatus for conditioning the aerosol has a separator for selecting a size of particles from an aerosol stream generated by the aerosol generator.

8. The device for aerosol generation according to claim 7, wherein the apparatus for conditioning the aerosol, with the separator, is connected via the first non-return valve and the first jet pump to the aerosol generator, such that the separator does not provide long-term storage for the particles separated as a liquid.

9. The device for aerosol generation according to claim 8, wherein the separator is a cyclone separator or a coalescent fiber separator.

10. The device for aerosol generation according to claim 9, wherein the separator and the collection container are components of a further chamber, such that the particles separated as liquid pass into the collection container by gravity.

11. The device for aerosol generation according to claim 1, wherein the separator and the collection container are components of a further chamber, such that the particles separated as liquid pass into the collection container by gravity.

12. The device for aerosol generation according to claim 1, wherein the first jet pump is a first injector pump, and the second jet pump is a second injector pump.

13. The device for aerosol generation according to claim 1, wherein the supply container, the collection container and/or the container has a fill level sensor or fill level sensors.

14. A method for aerosol generation without interruption when refilling, said method comprising using a device comprising:

a container holding a liquid, an aerosol generator with a supply container holding the same liquid, and an apparatus for conditioning with a collection container for receiving particles of an aerosol of the aerosol generator separated as liquid, and an outlet of for the aerosol, wherein the container, the aerosol generator, the apparatus for conditioning and the outlet are in a series connection, wherein the aerosol generator is connected to a pressurized gas generator, wherein the collection container is connected to the aerosol generator via a first non-return valve, configured to allow flow in a passage direction from the collection container to the aerosol generator, and a first jet pump, and wherein the container is connected to the aerosol generator via a second non-return valve, configured to allow flow in a passage direction from the container to the aerosol generator, and a second jet pump, wherein the opening pressure of the second non-return valve is greater than the pressure difference between the supply container of the aerosol generator and the surroundings of the device for aerosol generation and smaller than a pressure difference generated by the second jet pump during operation.

* * * * *